United States Patent
Zumkehr et al.

(10) Patent No.: US 12,279,818 B2
(45) Date of Patent: Apr. 22, 2025

(54) OPHTHALMOLOGIC MICROSCOPE WITH AT LEAST ONE CONTROLLED MANUAL DEGREE OF FREEDOM

(71) Applicant: Haag-Streit AG, Köniz (CH)

(72) Inventors: Frank Zumkehr, Köniz (CH); Jörg Breitenstein, Köniz (CH); André Huber-Meznaric, Köniz (CH); Thomas Killer, Köniz (CH); Julian V. Kool Van Langenberghe, Köniz (CH)

(73) Assignee: Haag-Streit AG, Köniz (CH)

( * ) Notice: Subject to any disclaimer, the term of this patent is extended or adjusted under 35 U.S.C. 154(b) by 631 days.

(21) Appl. No.: 17/621,924

(22) PCT Filed: Jun. 24, 2019

(86) PCT No.: PCT/EP2019/066676
§ 371 (c)(1),
(2) Date: Dec. 22, 2021

(87) PCT Pub. No.: WO2020/259794
PCT Pub. Date: Dec. 30, 2020

(65) Prior Publication Data
US 2022/0225870 A1    Jul. 21, 2022

(51) Int. Cl.
*A61B 3/00*    (2006.01)
*A61B 3/02*    (2006.01)
(Continued)

(52) U.S. Cl.
CPC .......... *A61B 3/0075* (2013.01); *A61B 3/0008* (2013.01); *A61B 3/13* (2013.01); *A61B 3/14* (2013.01)

(58) Field of Classification Search
CPC ......... A61B 3/02; A61B 3/102; A61B 3/1025; A61B 3/0075; A61B 3/113; A61B 3/1015;
(Continued)

(56) References Cited

U.S. PATENT DOCUMENTS

| | | | |
|---|---|---|---|
| 2,999,422 A | * | 9/1961 | Papritz ................... A61B 3/135 351/221 |
| 4,833,382 A | | 5/1989 | Gibbs |

(Continued)

FOREIGN PATENT DOCUMENTS

| | | |
|---|---|---|
| EP | 2 721 995 | 4/2014 |
| JP | S63-055514 | 3/1988 |

(Continued)

OTHER PUBLICATIONS

Japan Reasons for Refusal conducted in counterpart Japan Appln. No. 2021-576684 (Mar. 29, 2023).
(Continued)

*Primary Examiner* — Dawayne Pinkney
(74) *Attorney, Agent, or Firm* — GREENBLUM & BERNSTEIN, P.L.C.

(57) ABSTRACT

The ophthalmologic microscope comprises a first component including a base and a stage, a second component including a pivotal arm and a microscope device, and a third component including a pivotal arm and a light source. The various components are mutually pivotal at a hinge. An electronically controlled brake and a position sensor are incorporated into the hinge. The brake controller of the microscope is adapted to interrupt a manual mutual displacement of the components in response to a signal from the position sensor in order to assist the user in properly aligning the components.

22 Claims, 3 Drawing Sheets

(51) Int. Cl.
*A61B 3/024* (2006.01)
*A61B 3/10* (2006.01)
*A61B 3/13* (2006.01)
*A61B 3/14* (2006.01)

(58) Field of Classification Search
CPC ....... A61B 3/1225; A61B 3/024; A61B 3/005; A61B 3/103; A61B 3/14; A61B 3/125; A61B 3/107
USPC ........ 351/208–210, 200, 205–206, 221–223, 351/245–246
See application file for complete search history.

(56) References Cited

U.S. PATENT DOCUMENTS

| | | | | |
|---|---|---|---|---|
| 5,667,186 | A | * | 9/1997 | Luber .................... G02B 7/001 248/550 |
| 5,825,531 | A | * | 10/1998 | Otomo .................. G02B 21/26 359/368 |
| 7,118,218 | B2 | | 10/2006 | Barker |
| 7,410,257 | B2 | | 8/2008 | Takeda |
| 9,364,146 | B2 | | 6/2016 | Uchiyama |
| 9,675,244 | B1 | | 6/2017 | Ren et al. |
| 2004/0100618 | A1 | * | 5/2004 | Barker .................. A61B 3/135 351/206 |
| 2004/0263102 | A1 | * | 12/2004 | Kraus ................. F16M 11/105 318/432 |
| 2005/0117207 | A1 | * | 6/2005 | Haisch ................... G02B 7/001 359/381 |
| 2006/0274444 | A1 | | 12/2006 | Haisch et al. |
| 2009/0244697 | A1 | * | 10/2009 | Tumpner ............. G02B 21/242 318/568.1 |
| 2011/0001931 | A1 | | 1/2011 | Davis |
| 2013/0205558 | A1 | * | 8/2013 | Sporer .................. F16M 11/10 29/407.01 |
| 2016/0238815 | A1 | * | 8/2016 | John .................... F16M 13/027 |
| 2017/0156588 | A1 | | 6/2017 | Ren et al. |
| 2017/0156591 | A1 | | 6/2017 | Berestka et al. |
| 2019/0151043 | A1 | * | 5/2019 | Wada ..................... G16H 30/40 |

FOREIGN PATENT DOCUMENTS

| | | |
|---|---|---|
| JP | H07-016239 | 1/1995 |
| JP | 2017-526507 | 9/2017 |
| JP | 2019-000358 | 1/2019 |
| JP | 2019-502434 | 1/2019 |

OTHER PUBLICATIONS

Int'l Search Report (Form PCT/IB/210) conducted in Int'l Appln. No. PCT/EP2019/066676 (Feb. 28, 2020).
Int'l Written Opinion (Form PCT/IB/237) conducted in Int'l Appln. No. PCT/EP2019/066676 (Feb. 28, 2020).

* cited by examiner

OPHTHALMOLOGIC MICROSCOPE WITH AT LEAST ONE CONTROLLED MANUAL DEGREE OF FREEDOM

TECHNICAL FIELD

The invention relates to an ophthalmologic microscope having a stand, a microscope device, at least a first and a second component manually movable in respect to each other, and a position sensor arranged to measure the relative position between the first and second components.

BACKGROUND ART

US 2011/0001931 describes a slit lamp microscope that can be manually moved, in respect to its stand, along two horizontal directions.

The device is equipped with electrically controlled brakes to brake any movements along these degrees of freedom. The user operates the brakes by actuating a switch on the device.

EP2721995 describes another slit lamp microscope having a setting-state acquiring part with a position sensor for measuring the angle of the illumination.

DISCLOSURE OF THE INVENTION

The problem to be solved by the present invention is to provide an ophthalmologic microscope of this type that has increased ease of use.

This problem is solved by the ophthalmologic microscope of claim 1.

Accordingly, the ophthalmologic microscope comprises at least the following elements:

A microscope device: The microscope device, or simply microscope, typically comprises a lens system for magnifying an image of the eye. It may further comprise a camera and/or an ocular.

At least a first component and a second component: These two components are manually movable in respect to each other, e.g. by being provided with a suitable linear or pivotal bearing between them.

A position sensor having a first sensor member arranged to measure a relative position between said first and second components: This first sensor member may e.g. include an angular or linear sensor. It generates an electronic signal indicative of the mutual position of the two components.

An electrically controlled brake. This brake comprises a primary brake member arranged between the first and second components.

A brake controller connected to the position sensor and the brake and adapted to operate the brake as a function of a reading of the position sensor.

This design of the microscope makes it possible to actuate the brake depending on the position of the two mutually movable components. Hence, even though the user can manually move the components, the device can assist in properly positioning them.

Advantageously, the "first component" is the base of the device or a stage translationally mounted to said base.

The "second component" may e.g. comprise the microscope or a light source of the microscope.

In an important application, the first and second component are pivotally movable in respect to each other. This is a common degree of freedom in the components of an ophthalmologic microscope, and it is expensive to motorize this degree of freedom. Hence, an assisted manual placement of the components provides great benefit to the user.

In an advantageous embodiment, the microscope comprises a third component, which may e.g. include a light source, manually movable in respect to the first component as well as to the second component. In this case, the brake comprises a secondary brake member arranged between the first and third component in order to generate an electrically controllable braking force between them. Further, the position sensor comprises a second sensor member arranged to measure the relative position between the first and third components.

The second sensor member can either make a direct measurement between the first and third component, or it may measure the relative position between the second and third component from which the relative position between the first and third component can be determined indirectly by combining it with the reading of the first sensor member.

The brake may further comprise two secondary brake members, with one secondary brake member arranged between the first and third component and the other secondary brake member between the second and third component. This allows to mutually fix any two of the three components to move them as a common unit against the remaining component.

The brake controller can be adapted to calculating the time to actuate the brake depending on a desired mutual position. In particular, the controller may comprise one or more storage positions for storing one or more desired brake positions. The current readings of the position sensor are compared to this brake position(s) in order to assist braking at these positions.

In order to improve braking accuracy, the brake controller may be further adapted to carry out the following steps:

Determining the speed of motion between the components; and

Calculating the actuation time to actuate the brake depending on the desired mutual position and the speed of motion.

This allows an at least partial compensation of the speed-dependent braking distance of the microscope.

The brake controller may also be adapted to calculate the time delay between (1) actuating the brake and (2) the motion between the components coming to a standstill. This time delay can then be used to determine a more accurate actuation time for the brake.

As described below, this allows determining the state of the device and/or the manner in how it is used, which in turn helps to improve the timing of the braking process. In particular, the brake controller may be adapted to:

Using a plurality of past measurements of braking processes to derive at least one parameter describing the braking distance of the brake.

Calculating the actuation time of the brake depending on this/these parameter(s).

Hence, the prediction of the braking distance can e.g. be adapted to the manual force a user employs to operate the device and/or to the state of the brake.

BRIEF DESCRIPTION OF THE DRAWINGS

The invention will be better understood and objects other than those set forth above will become apparent when consideration is given to the following detailed description thereof. This description makes reference to the annexed drawings, wherein.

MODES FOR CARRYING OUT THE INVENTION

Overview

Figure 1:
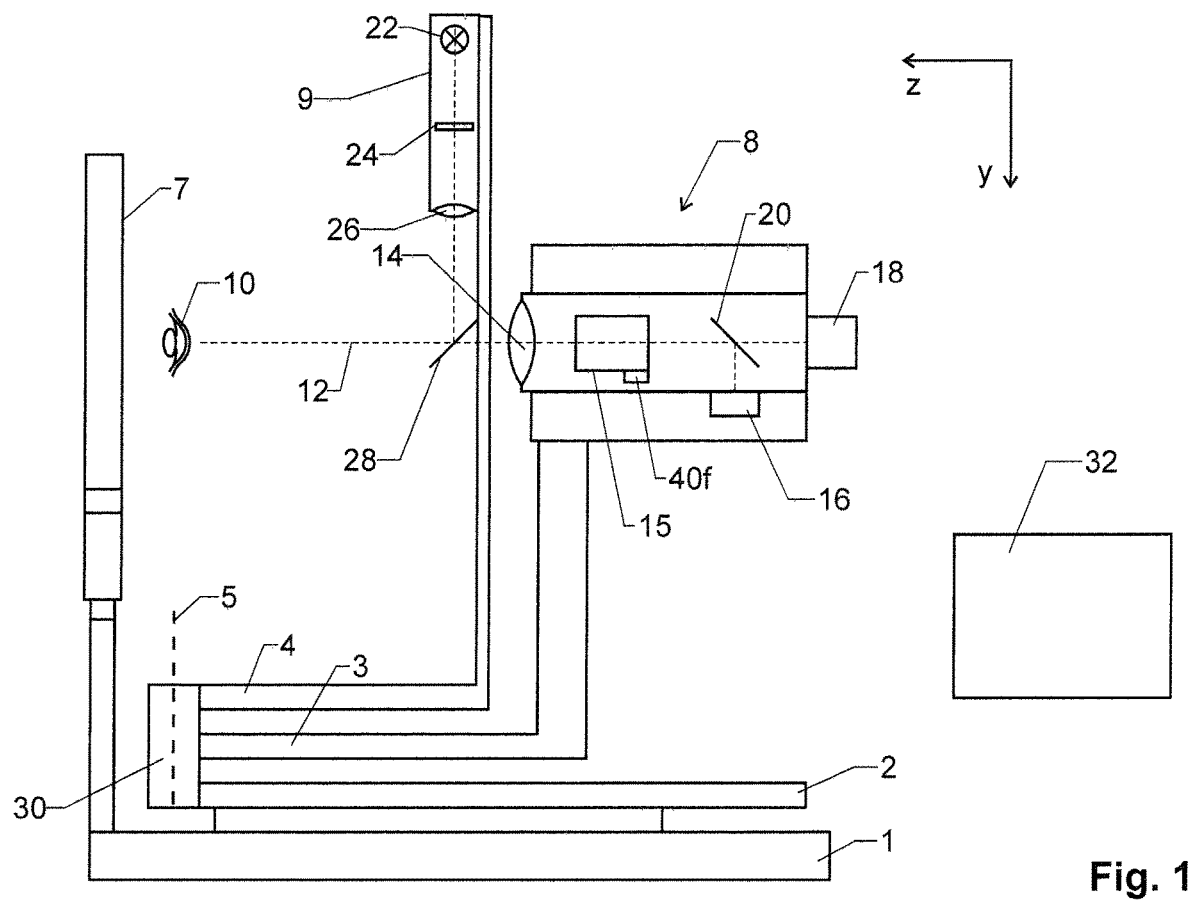
FIG. 1 shows a lateral view of a slit lamp microscope.
Figure 2:
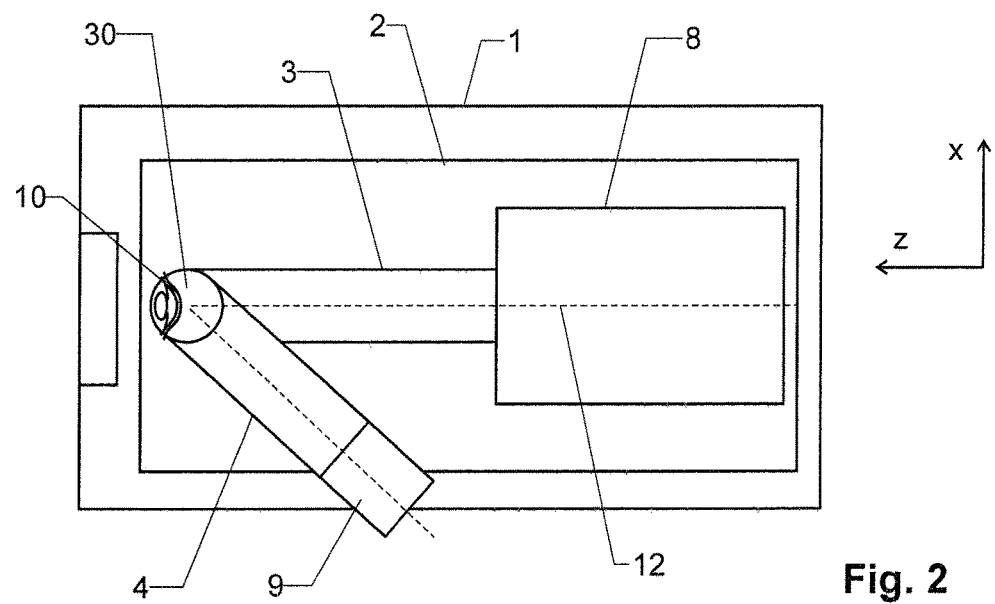
FIG. 2 shows a top view of the microscope (with the slit lamp arm pivoted in respect to the microscope's optical axis)

FIGS. 1 and 2 show an embodiment of an ophthalmologic microscope, in particular a slit lamp microscope.

The microscope has a base 1 resting e.g. on a desk, a translationally displaceable stage 2 mounted to base 1, a first arm 3, and a second arm 4.

Stage 2 can be linearly displaced along horizontal directions x and z in respect to base 1.

The arms 3 and 4 are mounted to stage 2 and pivotal about a common vertical pivot axis 5, i.e. an axis parallel to vertical direction y.

Advantageously, arms 3 and/or 4 are manually operated, i.e. their angular position is changed manually, and they are not equipped with electric actuators for changing their angular positions. They may, however, also be provided with electric angular actuators to operate them automatically in addition to manually.

The device may further include a headrest 7 mounted to base 1 for receiving the patient's head.

Arm 3 carries a microscope device 8, and arm 4 carries a light source 9.

Microscope 8 has an optical axis 12. It may comprise an entry objective 14, which projects an image of eye 10 onto a camera 16 and/or an eyepiece 18. A beam splitter 20 may be arranged to spilt light between these components.

Light source 9 may e.g. be a slit lamp as known to the skilled person, adapted to project a slit-shaped light beam onto the eye 10 to be examined. In the present embodiment, light source 9 comprises a light generator 22, a spatial light modulator or adjustable mechanical slit 24, and imaging optics 26.

Light generator 22 can e.g. comprise several units emitting different wavelengths, e.g. in the red, green, blue, and infrared range of the optical spectrum. These units can be controlled separately in order to change the color of light source 22. Imaging optics 26 projects the light from modulator 24 onto the anterior surface of eye 10, e.g. via a mirror 28 mounted to arm 4.

Light source 9 can be arranged above or below mirror 28.

The device further comprises a hinge 30 connecting the arms 3 and 4 and stage 2 as well as a brake controller 32 for operating a brake of the device.

These components are described in more detail below.

Hinge Design

Figure 3:
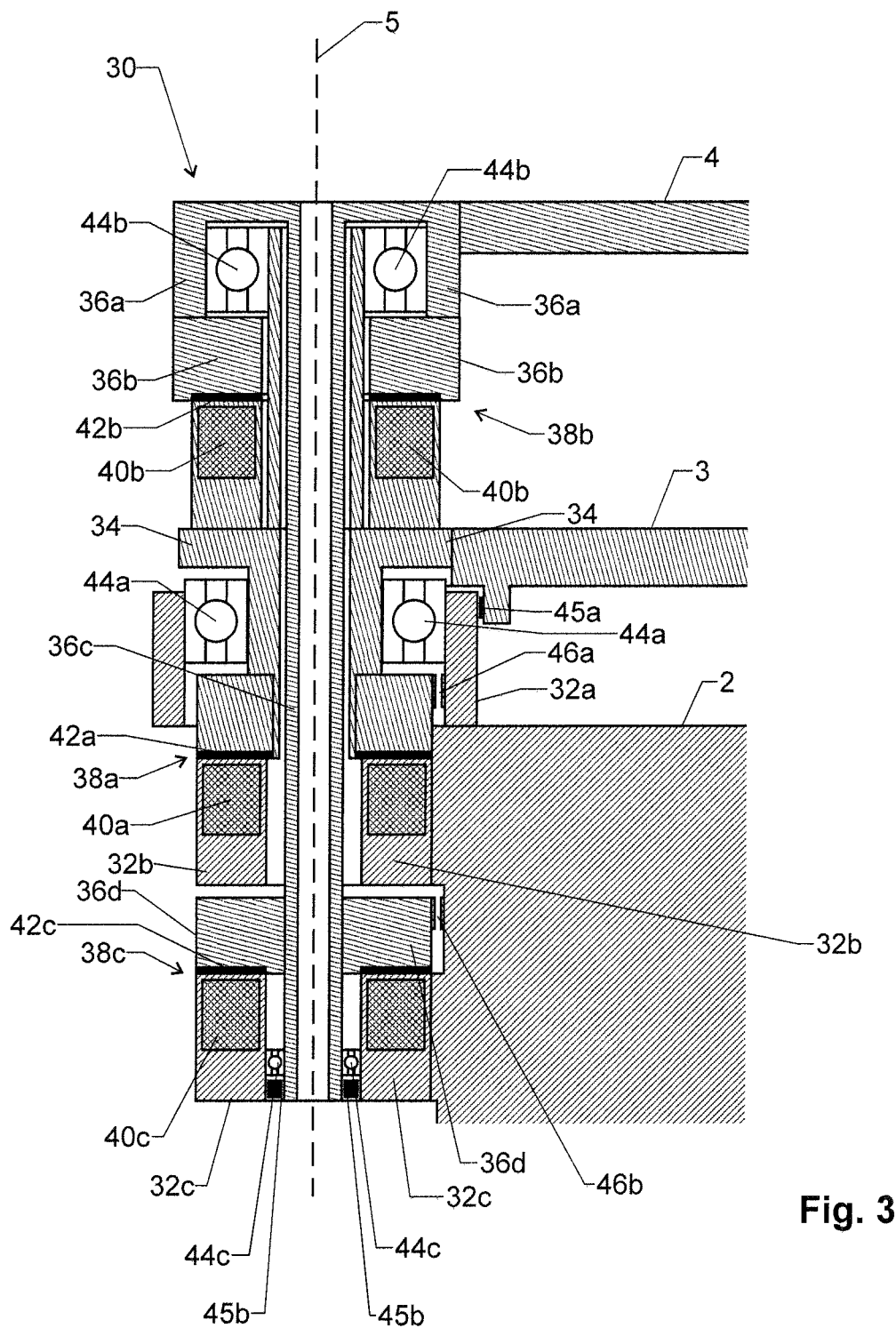
FIG. 3 shows a sectional view of a hinge.

FIG. 3 shows a schematic sectional view of hinge 30 along pivot axis 5. In this figure, parts with the same hatching style indicate parts that are rigidly connected to each other.

The purpose of Hinge 30 is to pivotally connect a first, a second, and a third component of the microscope to each other. In the present embodiment, the first component is stage 2, the second component is first arm 3 with microscope device 8, and the third component is second arm 4 with illumination source 9.

These three components are pivotal in respect to each other about pivot axis 5.

Hinge 30 comprises a "first hinge member" 32a, 32b, 32c rigidly connected to stage 2 (or base 1), i.e. to the first component of the microscope.

It further comprises a "second hinge member" 34 rigidly connected to arm 3, i.e. to the second component of the microscope.

It also comprises a "third hinge member" 36a-36d rigidly connected to arm 4, i.e. to the third component of the microscope.

For an embodiment of the invention where the components are pivotal, the term "rigidly" connected is to be understood as "non-pivotally" connected.

Hinge 30 further comprises a brake having a primary brake member 38a and one or two secondary brake members 38b, 38c.

Primary brake member 38a comprises a first coil member 40a and a first brake disk 42a, which are arranged to generate a frictional braking force between the first hinge member 32a-32c and the second hinge member 34.

In the embodiment shown, first coil member 40a is connected to first hinge member 32a-32c and first brake disk 42a is connected to second hinge member 34, even though the opposite arrangement can be used as well.

Secondary brake member 38b comprises a second coil member 40b and a second brake disk 42b, which are arranged to generate a frictional braking force between the second hinge member 34 and the third hinge member 36a-36d.

In the embodiment shown, second coil member 40b is connected to second hinge member 34 and second brake disk 42b is connected to third hinge member 36a-36d, even though the opposite arrangement can be used as well.

Secondary brake member 38c comprises a third coil member 40c and a third brake disk 42c, which are arranged to generate a frictional braking force between the first hinge member 32a-32c and the third hinge member 36a-36d.

In the embodiment shown, third coil member 40c is connected to first hinge member 32a-32c and third brake disk 42d is connected to third hinge member 36a- 36d, even though the opposite arrangement can be used as well. The brake members 38a, 38b, 38c can be actuated individually and independently.

The coil members 40a, 40b, 40c as well as brake disks 42a, 42b, 42c are advantageously annular and coaxially arranged round pivot axis 5.

The brake disks 42a, 42b, 42c are of a ferroelectric material, and they are attracted to their respective coil member 38a, 38b, 38c when a current is sent through the latter. In the shown embodiment, this attraction generates a frictional force that brakes the motion between the two respective hinge members.

Hinge 30 further comprises a primary pivotal bearing 44a pivotally connecting first hinge member 32a-32c and second hinge member 34. Its rotation axis coincides with pivot axis 5.

Hinge 30 also comprises two secondary pivotal bearings 44b, 44c. Secondary pivotal bearing 44b connects second hinge member 34 to third hinge member 36a-36d, and secondary pivotal bearing 44c pivotally connects first hinge member 32a-32c to third hinge member 36a 36d. The secondary pivotal bearings 44b, 44c are again coaxial to pivot axis 5.

Hinge 30 further comprises a position sensor with a first and a second sensor member 46a, 46b.

First sensor member 46a is arranged between first hinge member 32a-32c and second hinge member 34. It is adapted to measure the relative pivotal position between these two hinge members.

Second sensor member 46b is arranged between first hinge member 32a-32c and third hinge member 36a-36d. It is adapted to measure the relative pivotal position between these two hinge members.

The first and second sensor members 46a, 46b may be magnetic angular position sensors.

In the embodiment of FIG. 3, the first component of the microscope, i.e. stage 2 and/or base 1, is connected to a first location of hinge 30 (the lower end of hinge 30 in FIG. 3). The second component of the microscope, i.e. arm 3 and microscope device 8, is mounted to a second location of hinge 30 (the mid-section of the hinge in FIG. 3). The third component of the microscope, i.e. arm 4 and light source 9, is mounted to a third location of hinge 30 (the top end of the hinge in FIG. 3).

The second location is located, along pivot axis 5, between the first and third location. When using this type of design, the first hinge member 32a-32c or the third hinge member 36a-36d advantageously comprises a shaft extending through the second hinge member 34, which allows the first and third hinge members to interact directly.

In the embodiment of FIG. 3, this shaft 36c is formed by the third hinge member, which allows mounting secondary brake member 38c and/or second sensor member 46b at the first location of hinge 30.

In other words, the shaft is connected, at one side, to the first or third component of the microscope and, at the other side, to one of the brake members and/or sensors members.

Shaft 36c is hollow and can receive cabling, e.g. connected to the brake members 38a-38c, to microscope device 8, and/or to light source 9.

In the embodiment shown, the pivotal bearings 44a, 44b, 44c are roller bearings. Such roller bearings have very low friction when the brake is deactivated. This may not always be desirable. Hence, one or more frictional dampers 45a, 45b can be provided for damping the movement between at least one pair of the components.

The frictional damper(s) is/are designed to exert a permanent frictional force between the components, which is much larger than the roll resistance of the roller bearings, in particular at least 100 times larger.

In the embodiment shown, a first frictional damper 45a is provided for damping the movement between the first and second component, and a second frictional damper 45b is provided for damping the movement between the first and third component.

In more general terms, the device comprises the combination of at least one roller bearing and at least one frictional damper between at least two of the components.

Advantageously, there is a roller bearing 44a and a frictional damper 45a between the first and second component, and there is a roller bearing 44c and a frictional damper 45b between the first and third component. In a particularly advantageous embodiment, there is a roller bearing 44b but no frictional damper between the second and third component, which makes it easier to move the second or third component in respect to the first component without moving the third or second component, respectively.

Brake Operation

Figure 4:
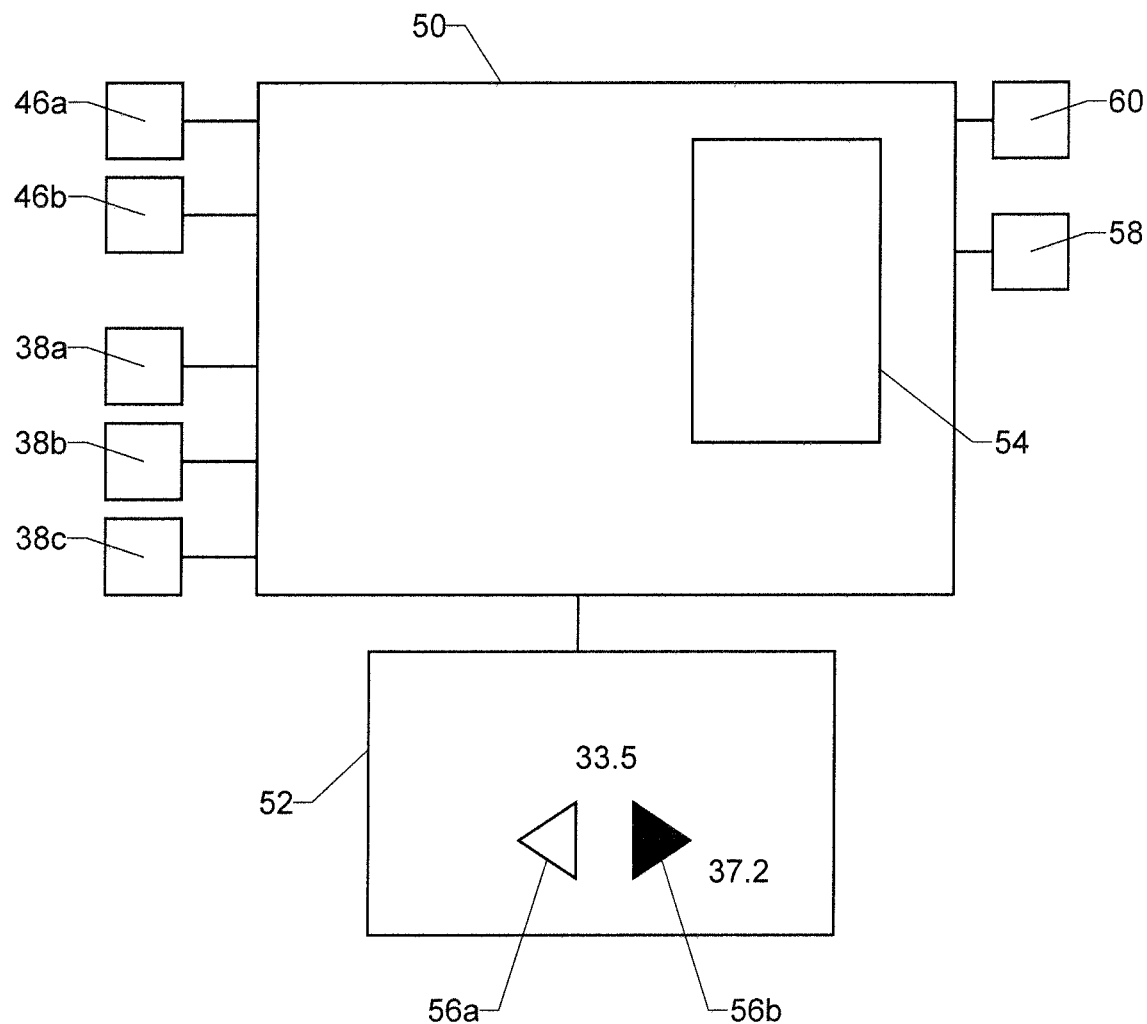
FIG. 4 shows a block circuit diagram of some components of the brake controller.

The microscope comprises a brake controller 50, which is schematically illustrated in FIG. 4.

It may comprise a microcontroller or microprocessor, which can e.g. be part of the control unit of the microscope. It is programmed to carry out the various brake functions described below.

Brake controller 50 is connected to the position sensor, i.e. to the sensor members 46a, 46b, which allows it to determine the current mutual positions of the three microscope components.

It is also connected to the brake members 38a, 38b, 38c to operate them.

Brake controller 50 is further connected to a display 52 adapted to show operating instructions and/or status information to the user.

In the following, we describe some functionalities that may be implemented in brake controller 50.

Actuation Time

A first functionality relates to supporting the user in moving the components of the microscope to a certain predefined mutual position.

In this functionality, a storage section 54 of brake controller 50 may hold at least one "desired mutual position" between two of the components of the microscope.

Brake controller 50 may now be equipped to compare this desired mutual position to the current mutual position between the two components. If there is a mismatch between the two, brake controller 50 displays, on display 52, the direction of displacement for moving one of the components to the desired mutual position.

For example, the desired mutual position may e.g. be an angle of 37.2° between stage 2 and first arm 3. First sensor member 46a e.g. indicates the current mutual position, i.e. the current angle, to be 33.5°. One or both of these numbers may be shown on display 52.

Next, brake controller 50 determines the direction to move arm 3 from its current position to the desired position. This direction is then displayed e.g. by highlighting one of two arrows 56a, 56b on display 52.

By displaying the direction of displacement in this manner, the user is assisted to manually move one of the components into the right direction.

Brake controller 50 may then assist the user further in properly braking the component being moved at the right time in order to stop the movement at the desired position. To do so, it calculates the time to actuate the brake, i.e. at least one of its brake members 38a, 38b, 38c.

In a most simple approach, the actuation time to activate the brake may be the one where the current position matches the desired position. This may, however, lead to a poor match because the brake has a certain braking distance and may therefore come to a halt at a position beyond the desired position.

A more accurate algorithm takes the speed of motion between the two components into account.

Let us assume that x0 is the desired mutual position and x(t) is the current mutual position. In that case, the actuation time t0 for actuating the brake should be the one where x0-x(t0) equals the expected braking distance D of the microscope, i.e.

$$x - x(t0) = D \qquad (1)$$

Braking distance D is not a constant. Rather, it is typically a function of the current speed $v(t)=dx(t)/dt$ of the motion and the reaction time Δt of the brake. It may also be a function of the force with which the user moves the component (a strong force may add to the braking distance). Hence $$D = D(\Delta t, v, u), \quad (2)$$

with u being a user-dependent parameter

In a specific example, braking distance D may be approximated by $$D = \Delta t \cdot v + u \quad (3)$$

The speed v in Eq. (2, 3) can be calculated from the measurements of the position sensor 46a, 46b. The parameters Δt and u may be obtained in various manner:

- The time delay Δt may be considered to be a device-specific delay, which can e.g. be obtained from calibration measurements at the manufacturer's site. However, it may vary over time, e.g. due to attrition or contamination of the brake, and it is therefore advantageously derived from prior braking processes as described below.
- The parameter u can be assumed to be constant and be determined from calibration measurements at the manufacturer's site with a sample of typical users. However, since it depends on how a given user operates the device, it is best also derived from prior braking processes (advantageously carried out by the same user as the one currently using the microscope) as described below.

If one or more of the parameters Δt, u is to be derived from previous braking processes, brake controller 50 is advantageously adapted to carry out the following steps:

- Measuring, for a plurality of past braking processes, the braking distance D and the speed v(t0) upon actuating the brake.
- Storing the braking distances and velocities obtained in this manner.
- Using a model for the braking distance D(Δt, v, u) as a function of the speed v(t0) having the unknown parameter(s) as model parameter(s) and fitting these model parameter(s) to the stored braking distances and velocities.

Depending on the model used for the braking distance D(Δt, v, u) as a function of the speed v(t0), it is e.g. possible to use a linear fitting algorithm (e.g. for the model of Eq. (3)) or a non-linear fitting algorithm.

If at least one parameter, such as parameter u, is to be varied between user and user, brake controller 50 is equipped with a suitable input means 58 for entering a user-specific ID. In that case, brake controller 50 determines different sets of parameters for the different users.

The determination of one or more parameters can e.g. be refined automatically after each braking process.

Releasing the Brake

The brake may be released manually, e.g. by providing a brake release input 60, such as a button or an area on a touchscreen. When the user operates this input, the brake is released.

In another embodiment, brake controller 50 may be adapted to carry out the following steps:

a) Detecting, while having activated the brake 38a, 38b, 38c, an increase of a force acting against the brake 38a, 38b, 38c.

b) Upon such an increase, releasing the brake 38a, 38b, 38c.

In this manner, the user may simply push one of the components against the force of the brake, in which case the brake is released.

Step a) and or b) may be suppressed for a given time, e.g. 1 second, after actuating a brake, or be suppressed while the component has not yet come to a standstill, in order to make sure that the force is an intentional effort to move the component away from its position after a completed braking process.

The detection of step a) may e.g. be carried out by means of a dedicated force sensor. However, if position sensor 46a, 46b is of sufficient resolution, it can be used to detect an elastic deformation in hinge 30 due to the force applied to the component(s), so it can be used to detect the force without the need for a dedicated force sensor.

Haptically Marking Positions

The brake can also be operated only briefly, in a "tapping" operation, while the user moves one of the components. This will generate a haptic feedback for the user that marks certain preferred mutual positions of the components, such as an axial alignment or an alignment under certain angles.

In order to implement this, brake controller 50 may be adapted to activating and automatically deactivating the brake 38a, 38b, 38c for a duration of less than 1 second, in particular of less than 0.5 seconds. On the other hand, the activation duration is advantageously at least 0.1 seconds because much slower activations may not be sufficient to generate a breaking effect the user can act upon.

The duration may e.g. be given as follows:

- It may be a fixed time.
- It may depend on the signal from the position sensor 46a, 46b. If, for example, brake controller 50 detects that the speed v(t) drops quickly after actuating the brake (e.g. by more than a given percentage in a given time), it can keep the brake activated, assuming that the user has released the component and wants to stop at this location. Otherwise, it releases the brake, assuming that the user has not released the component, does not want to stop at the given position, and wants to continue moving the component.

Such haptic feedback implemented by temporarily actuating the brake may eliminate the need for mechanical feedback members, such as mechanical indexing mechanisms.

Group Operation

Brake controller 50 may further be equipped for grouping two of the three components into a group while letting the remaining component free to move relative to the group.

For example, brake controller 50 may be adapted to operate the brake 38a, 38b, 38c in at least one, in particular at least two, of the following modes:

- Actuating first brake member 38a while deactivating second brake member 38b and third brake member 38c. In this case, the mutual position of the first and the second components (base 2 and arm 3 in the embodiment of FIG. 3) is kept fixed while the third component (arm 4) can be moved.

Actuating second brake member 3 8*b* while deactivating first brake member 38*a* and third brake member 38*c*. In this case, the mutual position of the second and third components (arms 3 and 4) is fixed, and the two can be moved as a group in relation to the first component (base 2).

Actuating third brake member 38*c* while deactivating first brake member 38*a* and second brake member 38*b*. In this case, the mutual position of the first and third components (base 2 and arm 4) is fixed, while the second component (arm 3) can be moved relation to them.

In other words, brake controller 50 may be adapted to keep one brake member activated while keeping the two other brake members deactivated, and, advantageously, the user may chose the brake member to be activated.

Notes

In the shown embodiment, the brake members are brought into their braking state by feeding a current through them. In other words, if the microscope is without current, the brake is released. This allows for a compact design of the device and/or reduces power consumption in the non-braking state.

In another embodiment, the brake members may be designed such that they are brought into their non-braking state by sending an electric current through them. This can e.g. be achieved by brake members having two rings urged against each other by a spring member, with an electromagnet that can be activated to act against the force of the spring. This design allows locking the microscope in the unused state in the absence of a current, and it reduces power consumption in the braking state.

In the embodiment above, there are three mutually movable components. The microscope may, however, also comprise only two mutually movable components, or it may comprise more than three of them.

In the shown examples, the components are pivotal in respect to each other, and the brake is adapted to brake the pivotal movement between the components. However, the invention may also be used for other types of relative displacement. It may e.g. be used to brake a linear displacement between components of the microscope, such as the displacement of stage 2 in respect to base 1 in the directions x and/or z or a vertical displacement of a component along direction y, such as a vertical displacement of headrest 7.

The microscope described here assists the user in properly aligning the various components, e.g. in order to establish or reproduce a desired measurement configuration.

While there are shown and described presently preferred embodiments of the invention, it is to be distinctly understood that the invention is not limited thereto but may be otherwise variously embodied and practiced within the scope of the following claims.

The invention claimed is:

1. An ophthalmologic microscope comprising:
   a microscope,
   at least a first component and a second component manually pivotally movable in respect to each other,
   a position sensor having a first sensor member arranged to measure a relative position between said first and second components,
   an electrically controlled brake having a primary brake member arranged between said first and second component, and
   a brake controller connected to said position sensor and said brake, and structured and arranged to operate said brake as a function of a reading of said position sensor.

2. The ophthalmologic microscope of claim 1, wherein:
   said first component is a base of said microscope or a stage translationally mounted to said base.

3. The ophthalmologic microscope of claim 1, wherein:
   said second component comprises said microscope.

4. The ophthalmologic microscope of claim 1, wherein:
   said second component comprises a light source.

5. The ophthalmologic microscope of claim 1, further comprising:
   a hinge connecting said first and said second component, wherein said hinge comprises:
      a first hinge member rigidly connected to said first component,
      a second hinge member rigidly connected to said second component, and
      a primary pivotal bearing having a pivot axis and connecting said first and said second hinge members.

6. The ophthalmologic microscope of claim 5, wherein:
   said hinge further comprises a first coil member and a first brake disk arranged around said pivot axis and positioned to generate a frictional braking force between said first and second hinge members depending on a current in said first coil member.

7. The ophthalmologic microscope of claim 1, further comprising:
   a third component manually pivotally movable in respect to said first component as well as to said second component, wherein;
   said brake comprises a secondary brake member arranged between said first and third component and/or between said second and third component and
   said position sensor comprises a second sensor member arranged to measure a relative position between said first and third components.

8. The ophthalmologic microscope of claim 5, further comprising:
   a third component manually pivotally movable in respect to said first component as well as to said second component, wherein:
   said brake comprises a secondary brake member arranged between said first and third component and/or between said second and third component and
   said position sensor comprises a second sensor member arranged to measure a relative position between said first and third components,
   wherein the hinge comprises:
      a third hinge member rigidly connected to said third component and
      a secondary pivotal bearing connecting said first or second hinge member and said third hinge member.

9. The ophthalmologic microscope of claim 8, wherein:
   said first and second component are pivotally movable in respect to each other,
   said microscope comprises a hinge connecting said first and said second component, wherein said hinge comprises:
      a first hinge member rigidly connected to said first component,
      a second hinge member rigidly connected to said second component, a primary pivotal bearing having a pivot axis and connecting said first and said second hinge members, a first coil member and a first brake disk arranged around said pivot axis and positioned to generate a frictional braking force between said first and second hinge members depending on a current in said first coil member, a second coil member and a second brake disk arranged around said pivot axis and positioned to generate a frictional braking force between said second and third hinge members depending on a current in said second coil member.

10. The ophthalmologic microscope of claim 8, further comprising:

a third coil member and a third brake disk arranged around said pivot axis and positioned to generate a frictional braking force between said first and third hinge members depending on a current in said third coil member.

11. The ophthalmologic microscope of claim 7, wherein:

said brake comprises two secondary brake members, with one secondary brake member arranged between said first and third components and the other secondary brake member between said second and third components.

12. The ophthalmologic microscope of claim 7, wherein:

said first and second component are pivotally movable in respect to each other, said microscope comprises a hinge connecting said first and said second component, wherein said hinge comprises:

a first hinge member rigidly connected to said first component, a second hinge member rigidly connected to said second component, and a primary pivotal bearing having a pivot axis and connecting said first and said second hinge members, wherein said first component is connected to a first location of said hinge, said second component is connected to a second location of said hinge, and said third component is connected to a third location of said hinge, wherein said second location is located between said first and said third location, and wherein said first hinge member or said third hinge member comprises a shaft extending through said second hinge member.

13. The ophthalmologic microscope of claim 1, wherein:

said brake controller is structured and arranged to calculate an actuation time to actuate said brake depending on a current mutual position and a desired mutual position.

14. The ophthalmologic microscope of claim 1, further comprising:

a display, and wherein said brake controller is structured and arranged to determine a current position between said components in relation to a desired mutual position, and indicating, on said display, a direction of displacement for moving one of the components to said desired mutual position.

15. The ophthalmologic microscope of claim 1, further comprising:

a roller bearing and a frictional bearing between at least two of the components.

16. The ophthalmologic microscope of claim 1, wherein:
said microscope is a slit lamp microscope having a slit lamp.

17. The ophthalmologic microscope of claim 10, wherein:

said first, second, and third coil members and said first, second, and third brake disks are arranged at different positions along said pivot axis.

18. An ophthalmologic microscope comprising:

a microscope, at least a first component and a second component manually pivotally movable in respect to each other, a position sensor having a first sensor member arranged to measure a relative position between said first and second components, an electrically controlled brake having a primary brake member arranged between said first and second component, a brake controller connected to said position sensor and said brake and structured and arranged to operate said brake as a function of a reading of said position sensor, said brake controller being structured and arranged to calculate an actuation time to actuate said brake depending on a current mutual position and a desired mutual position, and wherein said brake controller is structured and arranged to determine a speed of motion between said components, and calculate a time to actuate said brake depending on the desired mutual position and the speed of motion.

19. The ophthalmologic microscope of claim 18, wherein:

said brake controller is structured and arranged to calculate a braking distance between actuating said brake and the motion between said components coming to a standstill, and using said braking distance to determine a said actuation time.

20. The ophthalmologic microscope of claim 19, wherein:

said brake controller is structured and arranged to calculate an actuation time to actuate said brake depending on a current mutual position and a desired mutual position, using a plurality of past measurements of braking processes to derive at least one parameter describing the braking distance of said brake, calculate the actuation time depending on said usage parameter(s).

21. The ophthalmologic microscope of claim 1, wherein:

said brake controller is structured and arranged to detecting, while having activated said brake, an increase of force acting against said brake, and upon such increase, releasing said brake, wherein the position sensor is used for detecting said force.

22. An ophthalmologic microscope comprising:

a microscope, at least a first component and a second component manually movable in respect to each other a position sensor having a first sensor member arranged to measure a relative position between said first and second components, an electrically controlled brake having a primary brake member arranged between said first and second component, and a brake controller connected to said position sensor and said brake, and structured and arranged to operate said brake as a function of a reading of said position sensor, wherein said brake controller is structured and arranged to temporarily activate said brake by activating and automatically deactivating said brake for a duration of less than 1 second, in particular of less than 0.5 seconds.

\* \* \* \* \*